US00PP20189P2

(12) United States Plant Patent
Geerlings

(10) Patent No.: US PP20,189 P2
(45) Date of Patent: Jul. 28, 2009

(54) ***PHLOX* PLANT NAMED 'ALEXANDRA'**

(50) Latin Name: *Phlox paniculata*
Varietal Denomination: Alexandra

(75) Inventor: Peter Geerlings, Hillegom (NL)

(73) Assignee: Compass Plants B.V., Hillegom (NL)

( * ) Notice: Subject to any disclaimer, the term of this patent is extended or adjusted under 35 U.S.C. 154(b) by 0 days.

(21) Appl. No.: 12/214,214

(22) Filed: Jun. 16, 2008

(51) Int. Cl.
*A01H 5/00* (2006.01)

(52) U.S. Cl. ..... Plt./320
(58) Field of Classification Search ..... Plt./320
See application file for complete search history.

*Primary Examiner*—Annette H Para
(74) *Attorney, Agent, or Firm*—C. A. Whealy

(57) ABSTRACT

A new and distinct cultivar of *Phlox* plant named 'Alexandra', characterized by its upright plant habit; freely flowering habit; dark pink and white bi-colored flowers; and good cut flower and garden performance.

2 Drawing Sheets

Botanical designation: *Phlox paniculata.*
Cultivar denomination: 'Alexandra'.

BACKGROUND OF THE INVENTION

The present invention relates to a new and distinct cultivar of *Phlox,* botanically known as *Phlox paniculata* and hereinafter referred to by the name 'Alexandra'.

The new *Phlox* originated from a cross-pollination of two unnamed proprietary selections of *Phlox paniculata,* not patented. The new *Phlox* was discovered and selected by the Inventor as a single flowering plant from within the progeny of the stated cross-pollination grown in a controlled greenhouse environment in Hillegom, The Netherlands in July, 2004.

Asexual reproduction of the new *Phlox* by cuttings in a controlled greenhouse environment in Haarlem, The Netherlands since 2006, has shown that the unique features of this new *Phlox* are stable and reproduced true to type in successive generations.

SUMMARY OF THE INVENTION

Plants of the new *Phlox* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Alexandra'. These characteristics in combination distinguish 'Alexandra' as a new and distinct cultivar of *Phlox:*

1. Upright plant habit.
2. Freely flowering habit.
3. Dark pink and white bi-colored flowers.
4. Good cut flower and garden performance.

Plants of the new *Phlox* and the parent selections differ primarily in plant height and flower color.

Plants of the new *Phlox* can also be compared to plants of *Phlox paniculata* 'Laura', not patented. In side-by-side comparisons conducted in Hillegom, The Netherlands, plants of the new *Phlox* and 'Laura' differed primarily in flower color as plants of 'Laura' had lilac and white bi-colored flowers. In addition, plants of the new *Phlox* were taller than plants of 'Laura'.

BRIEF DESCRIPTION OF THE PHOTOGRAPHS

The accompanying colored photographs illustrate the overall appearance of the new *Phlox,* showing the colors as true as it is reasonably possible to obtain in colored reproductions of this type. Colors in the photographs may differ slightly from the color values cited in the detailed botanical description which accurately describe the colors of the new *Phlox.*

The photograph on the first sheet comprises a side perspective view of a typical flowering plant of 'Alexandra' grown in a container.

The photograph at the top of the second sheet is a close-up view of typical flowers of 'Alexandra'.

The photograph at the bottom of the second sheet is a close-up view of a typical leaves of 'Alexandra'.

DETAILED BOTANICAL DESCRIPTION

The aforementioned photographs and following observations, measurements and values describe plants grown in Hillegom, The Netherlands, under commercial practice during the late summer and early autumn in an outdoor nursery with day temperatures ranging from 14° C. to 32° C. and night temperatures ranging from 5° C. to 15° C. Plants had been growing for two years when the photographs and description were taken. In the following description, color references are made to The Royal Horticultural Society Colour Chart, 2001 Edition, except where general terms of ordinary dictionary significance are used.

Botanical classification: *Phlox paniculata* 'Alexandra'.
Parentage:
*Female, or seed, parent.*—Unnamed proprietary selection of *Phlox paniculata,* not patented.
*Male, or pollen, parent.*—Unnamed proprietary selection of *Phlox paniculata,* not patented.
Propagation:
*Type.*—By cuttings.

*Time to initiate roots.*—About three weeks at 20° C.

*Root description.*—Fine, fibrous; white in color.

Plant description:

*Plant form/habit.*—Upright plant habit; narrow inverted triangle; moderately vigorous growth habit. Basally branching habit, about two to three basal branches per plant.

*Plant height.*—About 44.6 cm.

*Plant width* (*spread*).—About 32.3 cm.

*Lateral branches.*—Length: About 31.6 cm. Diameter: About 4.5 mm. Internode length: About 3.7 cm. Strength: Strong. Texture: Smooth, glabrous. Color: Close to N186C tinted with close to 144B.

Foliage description:

*Arrangement.*—Opposite, simple.

*Length.*—About 10.3 cm.

*Width.*—About 3.5 cm.

*Shape.*—Elliptic to narrowly ovate.

*Apex.*—Apiculate.

*Base.*—Obtuse to attenuate.

*Margin.*—Entire; slightly sinuate.

*Texture, upper and lower surfaces.*—Smooth, glabrous.

*Venation pattern.*—Pinnate.

*Color.*—Developing leaves, upper surface: Close to 137A flushed with close to N186A; towards the base, close to 143A. Developing leaves, lower surface: Close to 143A to 143B flushed with close to N186A. Fully expanded leaves, upper surface: Close to 137A; venation, close to 146C. Fully expanded leaves, lower surface: Close to 146B; venation, close to 146C.

*Petiole.*—Length: About 2 mm. Diameter: About 3.5 mm by 2 mm. Texture, upper and lower surfaces: Smooth, glabrous. Color, upper and lower surfaces: Between 144B and 146C.

Flower description:

*Flower type/habit.*—Single rotate and salverform flowers arranged in compound terminal panicles; flowers face upright and outward. Panicles roughly conical in shape. Freely flowering habit with about 100 flower buds and flowers developing per inflorescence.

*Fragrance.*—Moderately fragrant; sweet and pleasant.

*Natural flowering season.*—Continuously flowering from July until September in The Netherlands. Flowers not persistent.

*Postproduction longevity.*—Flowers last about ten days on the plant.

*Flower buds.*—Height: About 2.1 cm. Diameter: About 4 mm. Shape: Narrowly oblanceolate. Color: Close to 72A.

*Inflorescence height.*—About 17.5 cm.

*Inflorescence diameter.*—About 12.2 cm.

*Flower diameter.*—About 3.7 cm.

*Flower depth.*—About 2.9 cm.

*Petals.*—Quantity per flower: Typically five in a single whorl; petals fused at the base into a narrow tube. Length: About 3.7 cm. Lobe width: About 1.6 cm. Shape: Spatulate. Apex: Obtuse. Margin: Entire. Texture, upper and lower surfaces: Smooth, glabrous. Color: Developing petals, upper surface: Close to N66A to N66B; towards the base, close to 155C, color becoming closer to 84B to 84C with development; throat, close to N186D. Developing petals, lower surface: Close to 73A to 73B; tube, close to N79C. Fully expanded petals, upper surface: Close to N66B; towards the base, close to 155C; throat, close to N79C. Fully expanded petals, lower surface: Close to 75A to 75B; tube, close to N79B.

*Sepals.*—Quantity per flower: Typically five in a single whorl, fused towards the base; campanulate calyx. Length: About 1.2 cm. Width: About 1.5 mm. Shape: Lanceolate. Apex: Narrowly apiculate. Margin: Entire. Texture, upper and lower surfaces: Smooth, glabrous. Color, developing sepals, upper surface: Close to 147B. Color, developing sepals, lower surface: Close to N186A to N186B; towards the base, close to 144C. Color, fully expanded sepals, upper surface: Close to N186A to N186B; towards the base, close to 144C. Color, fully expanded sepals, lower surface: Close to N186A to N186B; towards the base, close to 144B.

*Peduncles.*—Length: About 13.1 cm. Diameter: About 3 mm. Angle: Erect to about 45° from vertical. Strength: Strong. Texture: Smooth, glabrous. Color: Close to 144B tinged with close to N186C.

*Pedicels.*—Length: About 5 mm. Diameter: About 1 mm. Angle: About 30° from vertical. Strength: Strong. Texture: Smooth, glabrous. Color: Close to 144B tinged with close to N186C.

*Reproductive organs.*—Stamens: Quantity per flower: Typically five; fused with petals in throat. Filament length: About 1 mm. Anther shape: Oblong. Anther length: About 2.5 mm. Anther color: Close to 11D. Pollen amount: Scarce to moderate. Pollen color: Close to 11D. Pistils: Quantity per flower: One. Pistil length: About 2 cm. Stigma shape: Three-parted. Stigma color: Close to 150C to 150D. Style length: About 1.8 cm. Style color: Close to 183C to 183D. Ovary color: Close to 143A.

*Seed/fruit.*—Seed and fruit development have not been observed.

Disease/pest resistance: Plants of the *Phlox* have not been observed to be resistant to pathogens and pests common to *Phlox*.

Garden performance: Plants of the new *Phlox* have been observed to have good garden performance and tolerate rain, wind and temperatures ranging from about −30° C. to about 30° C.

It is claimed:

1. A new and distinct *Phlox* plant named 'Alexandra' as illustrated and described.

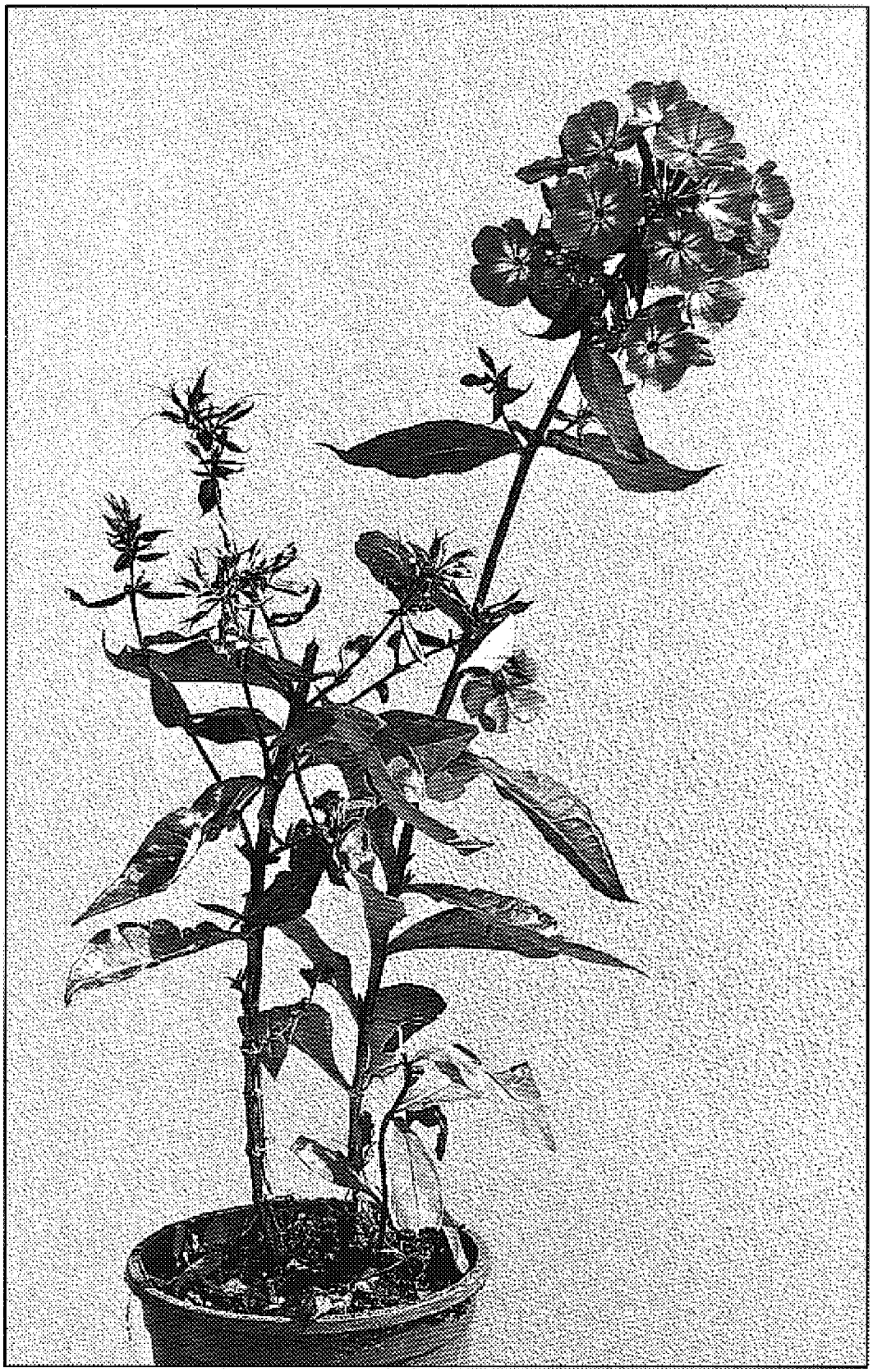

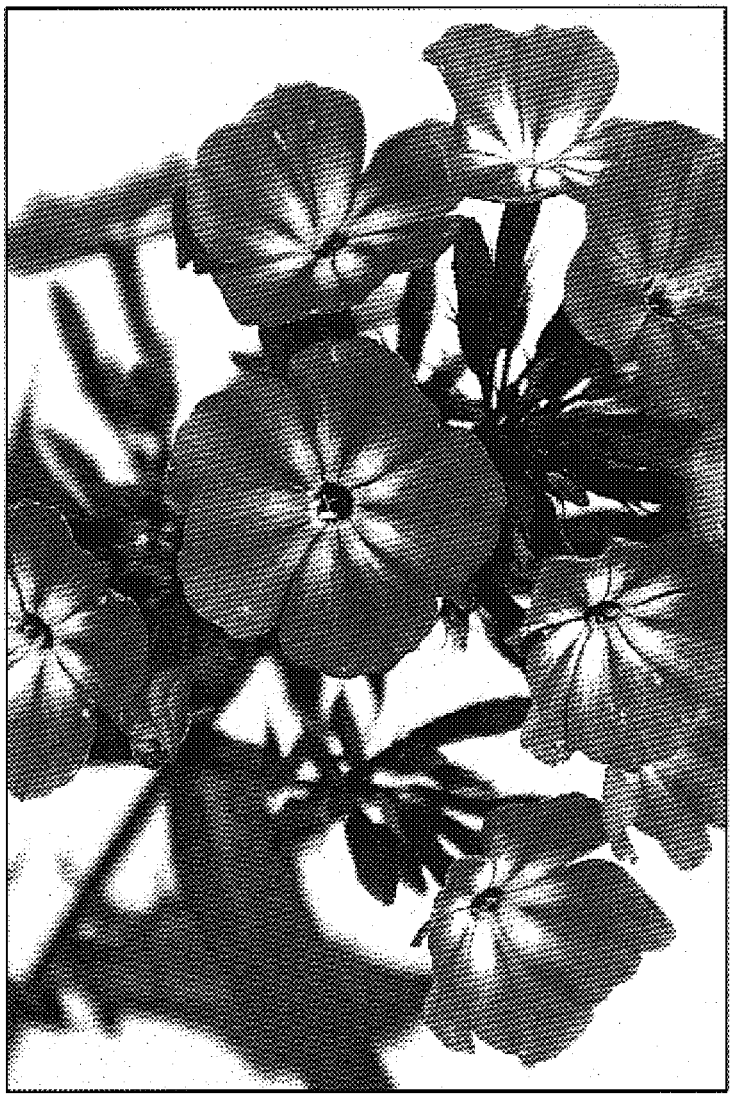
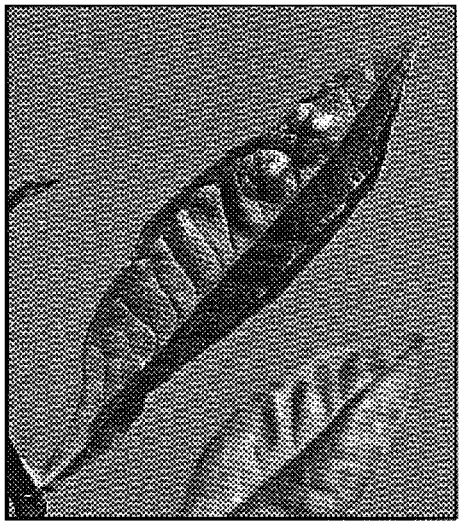

* * * * *